United States Patent
Fishel

(10) Patent No.: US 11,179,086 B2
(45) Date of Patent: Nov. 23, 2021

(54) AUTOMATED ELECTROANATOMICAL ANNOTATION OF POSITIVE ENTRAINMENT SITES FOR MAPPING OF ACTIVE REENTRANT CIRCUITS

(71) Applicant: Robert S. Fishel, Delray Beach, FL (US)

(72) Inventor: Robert S. Fishel, Delray Beach, FL (US)

( * ) Notice: Subject to any disclaimer, the term of this patent is extended or adjusted under 35 U.S.C. 154(b) by 114 days.

(21) Appl. No.: 16/131,306

(22) Filed: Sep. 14, 2018

(65) Prior Publication Data

US 2019/0076040 A1    Mar. 14, 2019

Related U.S. Application Data

(60) Provisional application No. 62/558,352, filed on Sep. 14, 2017.

(51) Int. Cl.
| | |
|---|---|
| *A61B 5/044* | (2006.01) |
| *A61B 5/04* | (2006.01) |
| *A61B 5/0464* | (2006.01) |
| *A61B 5/0468* | (2006.01) |
| *A61B 5/339* | (2021.01) |
| *A61B 5/00* | (2006.01) |
| *A61B 5/287* | (2021.01) |
| *A61B 5/341* | (2021.01) |

(Continued)

(52) U.S. Cl.
CPC .............. *A61B 5/339* (2021.01); *A61B 5/287* (2021.01); *A61B 5/341* (2021.01); *A61B 5/363* (2021.01); *A61B 5/364* (2021.01); *A61B 5/743* (2013.01); *A61B 5/7485* (2013.01); *A61B 5/7246* (2013.01); *A61B 2505/05* (2013.01)

(58) Field of Classification Search
CPC .. A61B 5/04011; A61B 5/0464; A61B 5/7246
See application file for complete search history.

(56) References Cited

U.S. PATENT DOCUMENTS

| | | | | |
|---|---|---|---|---|
| 6,088,614 | A | * | 7/2000 | Swanson ................. A61B 5/363 600/510 |
| 2007/0299355 | A1 | * | 12/2007 | Case ....................... A61B 5/363 600/510 |

(Continued)

FOREIGN PATENT DOCUMENTS

EP    1070480 A2    1/2001

OTHER PUBLICATIONS

Identification of Reentry Circuit Sites During Catheter Mapping and Radiofrequency Ablation of Ventricular Tachycardia Late After Myocardial Infarction. By: Stevenson et al. Published in Circulation vol. 88, Issue-4, Oct. 1, 1993 (Year: 1993).*

(Continued)

*Primary Examiner* — Gary Jackson
*Assistant Examiner* — Zahed Kabir
(74) *Attorney, Agent, or Firm* — Brown Rudnick LLP

(57) ABSTRACT

Method for determining positive entrainment sites for mapping active reentrant circuits, including the procedures of measuring a pre-entrainment cycle length at least one cardiac site, measuring a post-pacing interval (PPI) at the cardiac site, determining a difference between the PPI and the pre-entrainment cycle length and annotating the cardiac site according to the determined difference.

12 Claims, 6 Drawing Sheets
(5 of 6 Drawing Sheet(s) Filed in Color)

(51) Int. Cl.
 A61B 5/363 (2021.01)
 A61B 5/364 (2021.01)

(56) References Cited

U.S. PATENT DOCUMENTS

| | | |
|---|---|---|
| 2012/0078129 A1 | 3/2012 | Bailin |
| 2013/0096446 A1* | 4/2013 | Michael ................ A61B 5/316 600/510 |
| 2014/0243641 A1 | 8/2014 | Boveja et al. |
| 2015/0356742 A1 | 12/2015 | Barbarito et al. |
| 2016/0030743 A1* | 2/2016 | Kaiser ................ A61N 1/36514 607/14 |
| 2018/0103865 A1* | 4/2018 | Trayanova ............ A61B 5/0044 |

OTHER PUBLICATIONS

Challenges and Pitfalls of Entrainment Mapping of Ventricular Tachycardia. By: RoderickTung; Published in Circulation journal vol. 10 Issue-Apr. 4, 2017 (Year: 2017).*
Patel 2008 Circ Arrhythmia Electrophysiol; Atrial tachycardia after ablation of persistent atrial fibrillation: identification of the critical isthmus with a combination of multielectrode activation mapping and targeted entrainment mapping; vol. 1, No. 1; pp. 14-22.
Esato 2009 Heart Rhythm; Color-coded three-dimensional entrainment mapping for analysis and treatment of atrial macroeentrant tachycardia; vol. 6; No. 3; pp. 349-358.
Extended European Search Report dated Feb. 5, 2019 for EP Application No. 18194624.5, six (6) pages.
European Office Action issued in European Patent Application No. 18194624.5, dated Jan. 19, 2021, 5 pages.

* cited by examiner

AUTOMATED ELECTROANATOMICAL ANNOTATION OF POSITIVE ENTRAINMENT SITES FOR MAPPING OF ACTIVE REENTRANT CIRCUITS

CROSS-REFERENCE TO RELATED APPLICATIONS

This application claims the benefit of and priority to U.S. Provisional Application Ser. No. 62/558,352, filed Sep. 14, 2017, the contents of which are incorporated herein by reference.

FIELD OF THE DISCLOSED TECHNIQUE

The disclosed technique relates to complex ablation procedures in cardiac arrhythmias, in general, and to methods and systems for automating and enhancing the annotation of positive entrainment sites of active reentrant circuits, in particular.

BACKGROUND OF THE DISCLOSED TECHNIQUE

Cardiac arrhythmias are diseases affecting the electrical functioning of the heart which is responsible for sending the electrical pulses that cause the muscles of the heart to contract and to pump blood throughout the body. Various forms of arrhythmias relate to different characteristics of the cardiac electric circuit which in turn relate to different conditions of the pumping of the heart. Bradycardia, for example, relates to a condition wherein the heart beats too slowly, whereas tachycardia relates to a condition wherein the heart beats too fast. Cardiac fibrillation relates to a condition wherein muscles in the heart (either in the atria, ventricles or both) contract in a rapid, irregular and unsynchronized manner. Contraction of the muscles of the heart is effected by an electrical current originating in the upper chambers of the heart (i.e., the atria) which is propagated to the lower chambers of the heart (i.e., the ventricles). The electrical current originates in the sinoatrial (herein abbreviated SA) node, also known as the heart's natural pacemaker, which is a collection of cells located in the upper part of the right atrium of the heart that naturally generate electrical impulses. The electrical impulses produced by the SA node travel through the atria to the atrioventricular (herein abbreviated AV) node, which is a collection of cells in the interatrial septum separating the right and left atria and which acts as a relay or repeater for regulating the electrical impulses it receives and propagating them on further into the ventricles of the heart. Electrical impulses from the AV node are sent to the Purkinje fibers which line the inners walls of the ventricles and which propagate the electrical impulses throughout the ventricles thus causing them to contract. The electrical impulse which originates in the SA node and then travels to the AV node and finally into the Purkinje fibers is transferred from cell to cell in a relay action wherein a cell is polarized with electrical potential which is then depolarized as the electrical potential is transferred to a neighboring cell. Once a cell is depolarized it cannot immediately be repolarized with more electrical potential and must wait a refractory period wherein it is incapable of transferring more electrical potential. The refractory period in humans for heart cells is around 250 milliseconds (herein abbreviated ms). Electrical impulses propagate from the SA node to the AV node to the Purkinje fibers via pathways within the heart which can also be referred to as circuits for transferring electrical potential. The refractory period enables electrical impulses to travel in generally one direction, starting from the SA node towards the Purkinje fibers, while preventing electrical impulses from travelling in other directions. This enables the heart to pump in a synchronized manner, allowing blood to enter the heart and then exit it in a rhythmic manner.

Many arrhythmias are caused by a process known as reentry, in which electrical impulses repolarize recently depolarized cells. Therefore instead of travelling through the heart in one general direction and generating a rhythmic beating of the heart, an electrical impulse can cause parts of the heart to beat out of rhythm with its the general rhythm. As the name suggests, reentry is characterized by an electrical impulse which reenters a circuit in the heart that was already polarized. Reentry can be characterized by an electrical impulse which travels through the heart in a circular, almost racetrack like path. Reentry can also be characterized by other shapes of circuits in which electrical impulses repeatedly excite parts of the heart instead of depolarizing completely and only being repolarized when another electric impulse is generated by the SA node. These shapes can include a U-shape, a figure-eight shape and an L-shape. Paradoxically, although reentry is associated with rapid cardiac arrhythmias, reentry often occurs due to regions of relatively slowed conduction or regions of uni-directional conduction block. For example, reentry can occur because certain regions of the heart have cells which depolarize more quickly or more slowly than neighboring cells. In the case of cells which depolarize more quickly, these cells might repolarize from electrical current present in neighboring cells before the SA node has generated another electrical impulse, thereby causing parts of the heart to contract more frequently than the rate regulated by the SA node or AV node. In the case of cells which depolarize more slowly, an electrical impulse generated by the SA node reaching such cells might have to pass through a different circuit since these cells are still in their refractory period, thereby causing parts of the heart to beat out of sync. A premature electrical impulse can enter one branch of a potential circuit, can be blocked in one direction in the other branch, and even travel down the first branch and then enter the second branch only to reenter the first branch in a never ending circular fashion. Thus, due to the circularity of the electrical path the impulse travels around, electrical current running through the heart can get stuck in a never-ending circuit wherein the impulse continues to propagate, causing the heart to remain in a fixed, and typically, abnormally rapid rhythm. Reentry, in all its forms, is the most common cause of cardiac arrhythmias. The racetrack like path travelled by an electrical impulse in such a condition is known as a reentrant circuit, which is typically circular. As mentioned above reentrant circuits can also assume unusual shapes, such as oval shapes, figure-eight shapes and other atypical shapes. Reentry circuits can occur in both the atria and ventricles of the heart and are the predominant cause of rapid arrhythmias (such as tachycardia) in all four major chambers of the human heart. Reentry circuits can also occur in skeletal muscle, in brain tissue and in other electrical-biological circuits in the human body.

Reentry circuits typically occur near or in damaged cardiac tissue with delayed conduction causing improper conduction of electricity in the heart and leading to reentry circuits. For example, sudden cardiac death due to ventricular tachycardia is a common cause of death after a past heart attack and is commonly due to a reentry circuit in the left ventricle. With reference to FIG. 1, shown is a schematic illustration of a reentry circuit around a heart tissue, generally referenced 10, as is known in the prior art. FIG. 1 is an example of a typical cardiac reentry circuit in a heart tissue 12. An arrow 14 represents the path of an electrical impulse travelling towards heart tissue 12. When electrical impulse 14 arrives at heart tissue 12, it splits and travels down two separate paths, shown by arrows 16A and 16B. In normal heart tissue, the electrical impulse will continue travelling around heart tissue 12, meeting up at its other side and continuing on to another heart tissue, as shown by an arrow 20A. However heart tissue 12 may be damaged, as shown by a section 22, which effectively blocks (or delays) the conduction of electrical impulse 14 going down path 16B. This is shown schematically by an arrow 26 and an 'X' symbol in FIG. 1. When the electrical impulse travels down path 16A, as shown by an arrow 18, the electrical impulse splits again, travelling down path 20A yet also returning up the path electrical impulse 14 should have travelled down path 16B, shown as an arrow 20B. Section 22 enables conduction of the electrical impulse coming from path 20B, shown by an arrow 24. This is schematically shown by an arrow 28 and a '√' symbol in FIG. 1.

Since section 22 allows the electrical impulse along path 24 to conduct, the electrical impulse along path 24 may continue along path 16A after that section of heart tissue 12 has repolarized but before it has received another electrical impulse from the SA node or the AV node (both not shown), thereby causing the heart tissue to depolarize and sending the electrical impulse along path 16A again along path 24. This is thus a reentrant circuit. As shown, a counterclockwise reentrant circuit may be formed around heart tissue 12, causing it to beat rapidly since the reentrant circuit along path 24 may cause heart tissue 12 to beat a number of times before another electrical impulse is sent from the SA node or AV node. Section 22 thus represents a region of delayed conduction in heart tissue 12 that allows an electrical impulse to enter the reentry circuit (substantially shown as arrows 16A, 20B and 24) in one direction (counterclockwise in this example) and not the other. Once an electrical impulse enters the reentry circuit, the electrical impulse can propagate in a never-ending loop causing the heart to beat irregularly.

The typical treatment for a reentrant circuit is to ablate the reentrant circuit via an applied current which destroys the circuit and prevents reentry in the area of the heart where the circuit is located. Using the example of FIG. 1, this would mean ablating section 22 such that path 24 would no longer propagate an electrical impulse and section 22 would not allow electrical conduction in either direction. Prior to ablating the reentrant circuit, however, the reentry circuit must first be precisely located such that ablation is therapeutic. Ablating an area of the heart not directly on the reentrant circuit may not destroy the reentry circuit from functioning thus a precise location of the reentrant circuit must be located. Such procedures are known as complex ablation procedures and can take many hours or even an entire day given the need for determining the exact location of the reentry circuit in the heart.

As part of a complex ablation procedure, for example in the treatment of cardiac conditions associated with reentry such as supraventricular tachycardia, atrial reentry or ventricular tachycardia, an electroanatomical timing map is first constructed. Electroanatomical timing maps are known in the art and are usually colour-coded to aid a medical practitioner such as an electrophysiologist in interpreting the map and various rates at which electrical impulses travel through various circuits within the heart tissue. Electroanatomical timing maps are constructed as follows. A stable and fixed in position reference electrode (also known as a reference catheter) is maneuvered in the heart and positioned outside a reentrant circuit. The relative propagation times for an electrical impulse from the reference electrode and a potential reentrant circuit can then be measured. A second catheter, known as a mapping catheter is then introduced and the timing of electrical impulse arrival to this mapping catheter versus the stable reference catheter can then be measured. By moving the reference catheter and the mapping catheter around the heart, an entire map of the electrical conduction of the heart can be constructed. The mapping catheter typically also has a method to deliver destructive energy through its tip (and can thus be referred to as well as an ablation catheter). Most often radiofrequency (herein abbreviated RF) energy is delivered through the ablation catheter which heats and thus destroys the underlying tissue. If the catheter tip is on top of the reentrant circuit at this point in time, the arrhythmia should terminate and may be potentially cured. Various other types of destructive energy can be delivered via a mapping/ablation catheter during a catheter ablation procedure including heat, cold, chemicals and radiation.

The exact location of the mapping catheter within the heart can be determined via triangulation with external magnetic fields, via ultrasound triangulation to fixed ultrasound emitters or via impedance measurements of orthogonally delivered external electrical currents. These techniques have been previously described and are known in the field. At a given location, timing of a potential reentrant circuit is measured versus the electrical timing reference and a colour annotation can be used to create a map of the heart representing the electrical timing of the potential circuit. By moving the mapping electrode all around the heart, an electroanatomical timing map of the heart can be constructed. Reference is now made to FIG. 2, which is an example of an electroanatomical timing map showing possible reentrant circuits, generally referenced 40, as is known in the prior art. Two different electroanatomical timing maps 42A and 42B are shown. A colour legend 44 is shown on each electroanatomical timing map ranging from purple, dark blue and light blue to green, yellow and then red. The change in colour represents difference in relative conduction time of an electrical impulse as compared to the conduction time of an electrical impulse as measured by a reference catheter. In the examples given in FIG. 2, red represents a relative conduction time of zero milliseconds where up the colour legend towards purple represents longer relative conduction times. Electroanatomical timing maps 42A and 42B do not shown the location of reentrant circuits, they merely show the differences in conduction time of electrical impulses through and over the heart.

Potential reentrant circuits are determined manually or automatically via computer derived algorithms measuring the cycle length for an electrical impulse to travel through a circuit in the heart. For example, in a patient suffering from tachycardia, if the cycle length of the tachycardia is 350 ms, the actual reentrant circuit causing the tachycardia should also demonstrate a cycle length on the timing map with activation times that are within the potential circuit encompassing 350 ms as well. Determined circuits with shorter or longer activation times would not be considered as possibilities for the reentrant circuit causing the tachycardia. As shown in FIG. 2, electroanatomical timing maps have colours added to them to help an operator interpret the map. In a region of potential reentry, the earliest colour (zero time which in this example is indicated in red) would ultimately meet the latest colour (measured at the cycle length of the tachycardia, in this example 350 ms and shown in purple). FIG. 2 shows typical electroanatomical timing maps whereby colours representing early conduction times meeting colours representing late conduction times which suggest a possible region of reentry, as shown by arrows 46 and 48. It is noted that arrows 46 and 48 were added manually to the maps shown to illustrate the notion of potential reentrant circuits in an electroanatomical map. Such arrows are not automatically added by the software which generates the colour coding of the maps shown.

The reason these maps only represent possible and not definite regions of reentry is because the region mapped may simply be passively activated by a source of tachycardia originating elsewhere with the timing of the activation circuit that coincidentally matches the cycle length of the tachycardia. Thus the entirety of the maps in FIG. 2 might merely represent bystander circuits whose timing of activation of the circuit matches or is close to the cycle length of the tachycardia however which are unrelated to the actual reentrant circuit causing the tachycardia. Thus if the circuits as shown by arrows 46 and 48 were ablated, they may in fact not cause a termination of the reentrant circuit causing the tachycardia since those circuits may be simply bystander circuits.

As mentioned above, surgical resection of a bystander circuit with a scalpel or targeted disruption of the circuit with an ablation catheter or other tool able to interrupt conduction will not resolve the problem. To make matters more complicated, in many instances numerous potential reentrant circuits can be found in the same cardiac chamber with a detailed timing mapping, as an example of which is shown in FIG. 3. Reference is now made to FIG. 3, which is an example of an electroanatomical timing map showing many possible reentrant circuits on the same map, generally referenced 60, as is known in the prior art. FIG. 3 shows a colour-coded map of a heart chamber 62 with a colour legend 64. As illustrated manually, electroanatomical timing map 60 shown shows four potential active reentrant circuits 66A, 66B, 66C and 66D based on the annotated timing points. Each potential active reentrant circuit shows an area where the fastest conduction times meet the slowest conduction time. One of these circuits may be the cause of the patient's clinical cardiac arrhythmia or all may represent bystander circuits with the anatomical origin of the arrhythmia located elsewhere in the heart, perhaps in a different chamber.

The only way to determine definitively if a potential reentrant circuit is the reentrant circuit causing the arrhythmia is to perform entrainment of the circuit using overdrive pacing. Entrainment relates to the physical principle in which a rhythmic oscillation (for example, the rate of energy transfer) between two separate systems (for example, the human body and a surrounding environment) in proximity to one another sync up and effectively oscillate (for example, transfer energy) at a similar rate. An entrained circuit thus represents a circuit in the heart in which the rate of electrical conduction in the entrained circuit syncs up with an imposed electrical impulse from another system (such as an external pulse generator outside the heart). In the technique of circuit entrainment using overdrive pacing, a series of fixed rate pacing impulses slightly faster than the cycle length of the tachycardia is delivered via a mapping/ablation catheter. If the catheter happens to be inside the true reentrant circuit, it will capture and excite the reentrant circuit slightly faster than what the reentrant circuit shows during baseline tachycardia, thereby causing the reentrant circuit to entrain with fixed rate pacing impulse. Overdrive pacing is then stopped. If the catheter is pacing inside the reentrant circuit, the last impulse will make an entire loop around the reentrant circuit at the same cycle length of the baseline arrhythmia and will, upon traveling around the full circuit, be recorded by the mapping/ablation catheter on the first native reentrant cycle. If the timing of this circuit is the same as the cycle length of the tachycardia, then the mapping/ablation catheter is considered to be pacing from somewhere within the reentrant circuit and not external to it. The measurement of the amount of time it takes to see the next beat of tachycardia after the cessation of overdrive pacing occurs is termed in the art as the post-pacing interval (herein abbreviated PPI). PPIs of zero or up to 20 ms typically indicate that the mapping/ablation catheter is either within or extremely proximate to the true reentrant circuit causing the tachycardia. The PPI of a next beat of an arrhythmia can be determined by examining an electrocardiogram (herein abbreviated EKG). Reference is now made to FIG. 4, which is an EKG showing a reentrant circuit which is the cause of a tachycardia, generally referenced 80, as is known in the prior art. FIG. 4 shows an example where the TCL (tachycardia cycle length), as shown by an arrow 82, and the PPI, as shown by an arrow 84, are equivalent, both being 350 ms. Thus the position of the ablation catheter shows that it is positioned somewhere in an actual reentrant circuit causing tachycardia.

Reference is now made to FIG. 5, which is an example of two EKGs showing reentrant circuits which are not the cause of a tachycardia, generally referenced 90, as is known in the prior art. FIG. 5 shows two examples of EKGs, a first EKG 92A and a second EKG 92B, where a potential reentrant circuit is found but is eventually determined, using overdrive pacing, that these potential circuits are not the actual reentrant circuits causing a tachycardia. In EKG 92A, the mapping catheter is slightly outside of the reentrant circuit and requires 30 ms to enter the circuit and another 23 ms to exit the circuit. Thus, during attempts at entrainment with overdrive pacing, the PPI, as shown by an arrow 96A, is 282 ms, which is 47 ms longer than the tachycardia cycle length of 235 ms, as shown by an arrow 94A. A PPI of 282 ms is longer than the cycle length of the tachycardia and indicates that the mapping catheter is relatively close to the actual reentrant circuit but not within the circuit and destruction of tissue under the catheter-recording surface will not terminate the cardiac arrhythmia. In EKG 92B, the mapping catheter is far removed from the actual reentrant circuit. Here the PPI, as shown by an arrow 96B, is 388 ms which is 153 ms longer than the tachycardia cycle length of 235 ms, as shown by an arrow 94B. This indicates a region of entrainment pacing that is very poor and represents a site very far removed from the actual reentrant circuit causing the arrhythmia.

According to the prior art, in a complex ablation procedure, each potential reentrant circuit must be located using an electroanatomical timing map, entrainment of the circuit with overdrive pacing must be performed, the PPI is determined and a manual calculation must be made to determine if the PPI of the circuit indicates if the circuit is the reentrant circuit causing a tachycardia or not. Furthermore, as the electroanatomical timing map of the heart is constructed, the operator must manually indicate which reentrant circuits have PPIs which are within the range of being the actual reentrant circuit and which are not. This mode of generating an electroanatomical timing map for the purposes of complex ablation procedures is cumbersome and lengthy.

Prior art in the field includes US patent application publication numbers 2015/0356742, 2014/0243641 and 2012/0078129. For example, US patent application publication number 2015/0356742, issued to Barbarito et al. and entitled "COMPUTER IMPLEMENTED METHODS FOR IDENTIFYING CHANNELS IN A 3D VOLUME AND COMPUTER PROGRAM PRODUCT IMPLEMENTING THE METHODS" is directed to a method for the automatic detection of channels in a 3D data volume in internal organs for use in the fields of medicine and veterinary medicine. The method includes the procedures of obtaining a 3D volume of an object containing two different sub-volumes identified as a well-defined zone (S) sub-volume and a not-well-defined zone (BZ) sub-volume and generating well-defined zone patches and not-well-defined zone patches from the two sub-volumes. The method further includes the procedures of automatically identifying the possible channels by means of automatically obtaining candidate channels regions (CCRs) and dilating the perimeters of the well-defined zone patches. According to the method, this is achieved by dilating the perimeters of the zone S patches and considering as candidate channel points (CCPs) the perimeter points that intersect the perimeter of adjacent zone S patches and/or the perimeter points that intersect with the same perimeter of the same zone S patches before reaching a maximum dilation and that lie within a zone BZ patch. Determined adjacent CCPs can be used as CCRs. The method can be embodied using a layered approach, an electroanatomical mapping polygonal mesh approach and a volume approach.

US patent application publication number 2014/0243641, issued to Boveja et al. and entitled "METHODS AND SYSTEM FOR REAL-TIME CARDIAC MAPPING" is directed to a method and system for electroanatomical mapping which includes bringing a patient's image such as a fluoroscopic image and intracardiac signals into a computer based mapping system and is useful for diagnosing and for ablation treatment of various different types of cardiac arrhythmias. Electroanatomical mapping or superimposing of cardiac electrical activity on a fluoroscopic image is provided by placing visual indicators on electrode pairs of various catheters including standard catheters and an ablation catheter. The visual indicators are coupled or linked to underlying electric signals from those electrode pairs via software coding whereby electrical activity sequences of the heart are provided and updated in real-time on the fluoroscopic image. A combination of a fluoroscopic image and CT or MRI image may also be used.

US patent application publication number 2012/0078129, issued to Bailin and entitled "METHOD FOR DETERMINING THE LOCATION OF REGIONS IN TISSUE RELEVANT TO ELECTRICAL PROPAGATION" is directed to a method of displaying an image of the location of one or more low voltage structures in tissue in the body. The method includes receiving electrical mapping data corresponding to a portion of the tissue and generating an image using the electrical mapping data. Electrical mapping values within at least one voltage range having two endpoints that bound the upper and lower limits of the voltage range are distinguishable from electrical mapping values outside the voltage range. The two endpoints are selected to distinguish the one or more low voltage structures of the tissue from other portions of the tissue.

SUMMARY OF THE DISCLOSED TECHNIQUE

The disclosed technique provides for a novel method and system for mapping and annotating reentrant circuits having a post-pacing interval indicative of an actual reentry circuit causing tachycardia or other types of arrhythmia, which overcomes the disadvantages of the prior art.

According to one aspect of the disclosed technique, there is thus provided a method for determining positive entrainment sites for mapping active reentrant circuits. The method includes the procedures of measuring a pre-entrainment cycle length at least one cardiac site and measuring a post-pacing interval (PPI) at the cardiac site. The method also includes the procedures of determining a difference between the PPI and the pre-entrainment cycle length and annotating the cardiac site according to the determined difference.

According to another aspect of the disclosed technique, the method further includes the procedure of annotating the cardiac site on an electroanatomical map. According to a further aspect of the disclosed technique, the method further includes the procedure of redrawing the electroanatomical map with at least one active reentrant circuit being annotated on the electroanatomical map.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosed technique will be understood and appreciated more fully from the following detailed description taken in conjunction with the drawings in which.

DETAILED DESCRIPTION OF THE EMBODIMENTS

Figure 1:
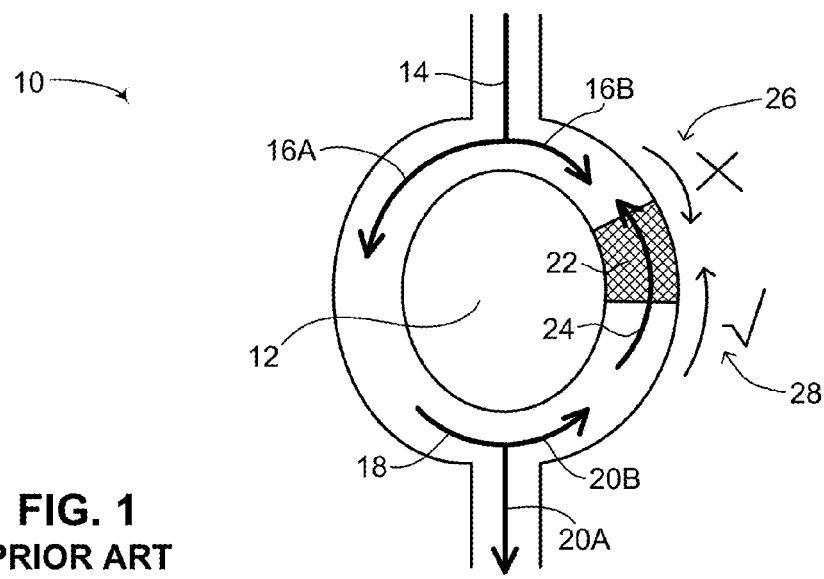
FIG. 1 is a schematic illustration of a reentry circuit around a heart tissue, as is known in the prior art.
Figure 2:
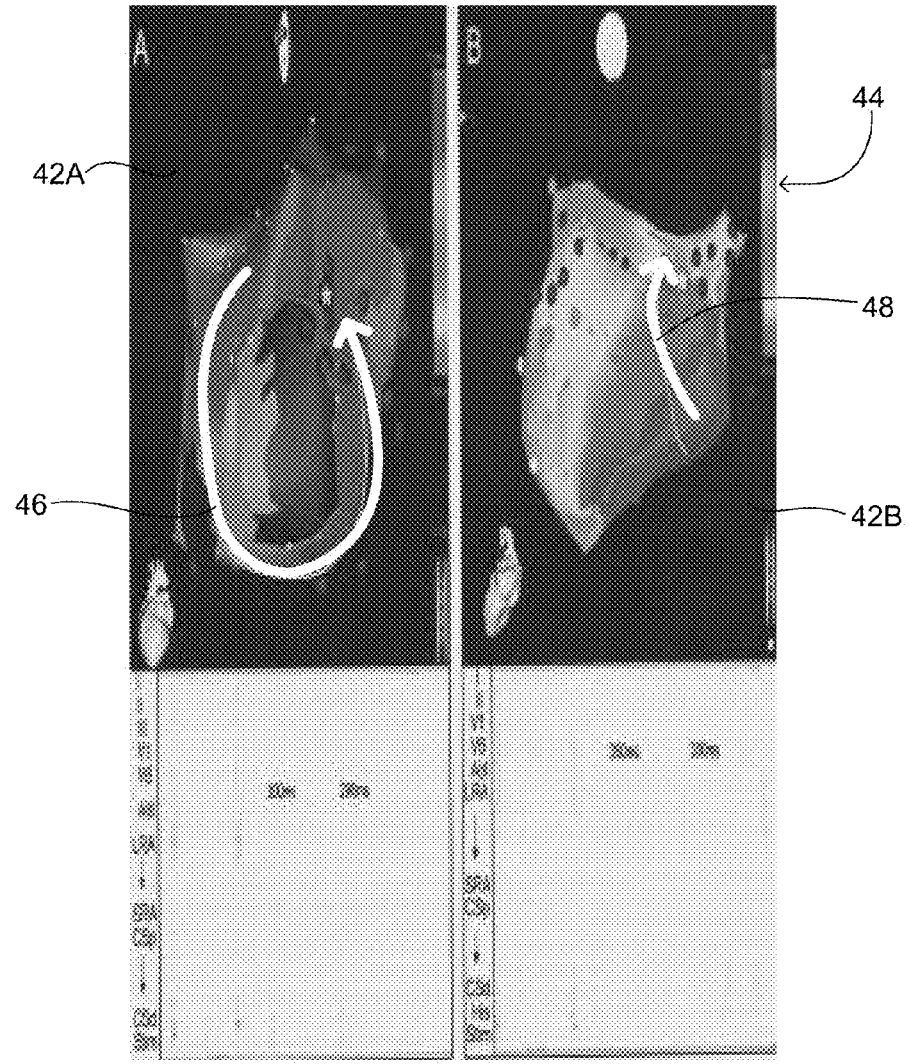
FIG. 2 is an example of an electroanatomical timing map showing possible reentrant circuits, as is known in the prior art.
Figure 3:
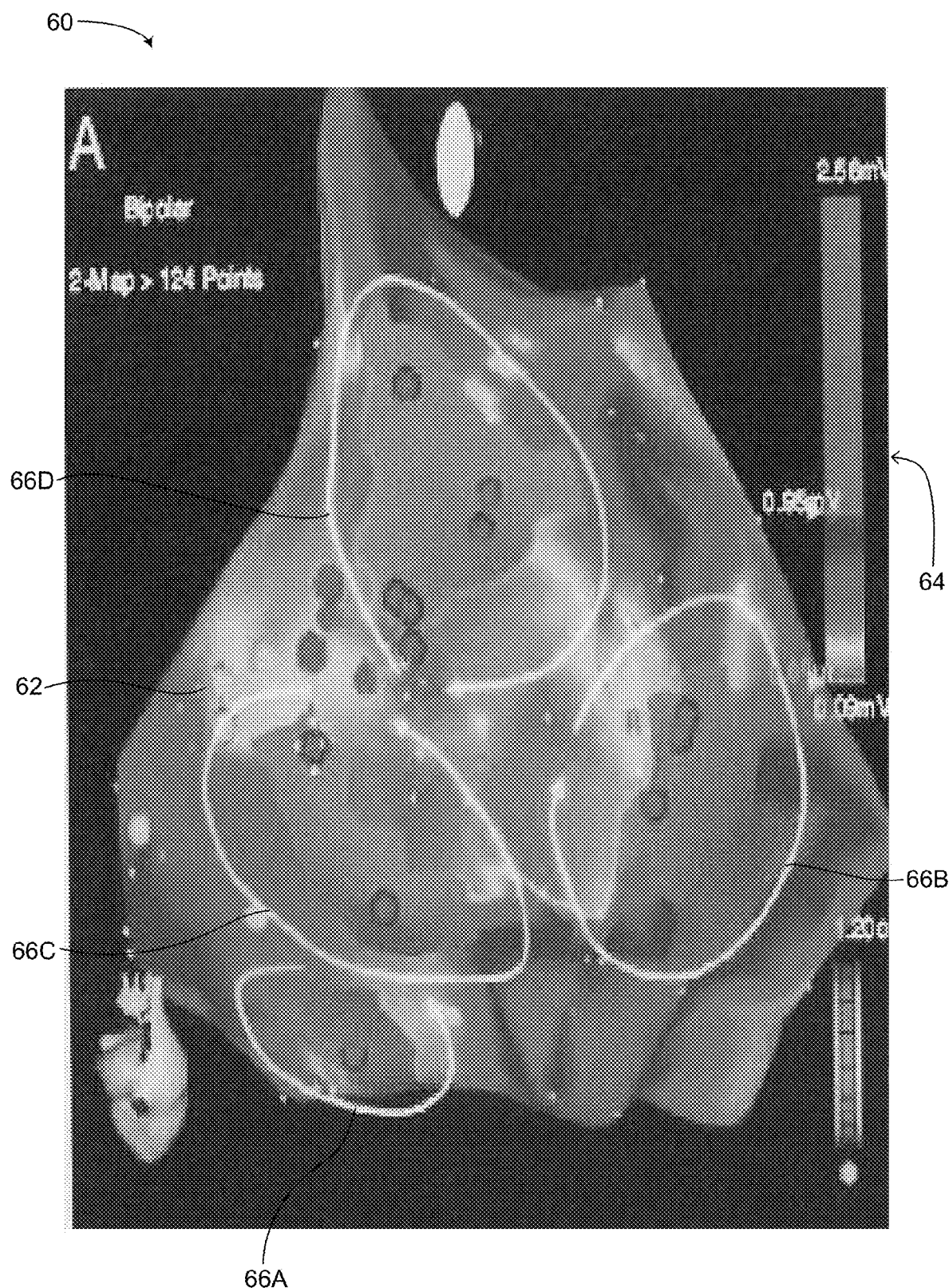
FIG. 3 is an example of an electroanatomical timing map showing many possible reentrant circuits on the same map, as is known in the prior art.

The disclosed technique overcomes the disadvantages of the prior art by providing an automated method and system for mapping and annotating reentrant circuits having a PPI indicative of an actual reentry circuit causing tachycardia or other type of arrhythmia. According to the disclosed technique, a measured PPI of a potential reentrant circuit is recorded and compared to a tachycardia cycle length. As mentioned above, a PPI measurement can be obtained using overdrive pacing. Depending on the difference between the tachycardia cycle length and the PPI, the potential reentrant circuit is annotated on an electroanatomical timing map. The annotation may be colour-coded or coded in another visual manner that depicts how likely the potential reentrant circuit is an active reentrant circuit causing tachycardia. By moving a mapping/ablation catheter around the heart of a patient, an enhanced electroanatomical timing map of the patient's heart can be determined showing not only the timing of electrical conduction within the heart but also the various reentrant circuits of the heart and which reentrant circuit(s) is most likely the cause of an arrhythmia. The disclosed technique enables the time required for mapping the electrical conduction of the heart in a complex ablation procedure to be significantly shorter.

According to the disclosed technique, a sensor in the tip of a mapping catheter or ablation catheter will automatically measure the PPI of an entrained potential reentry circuit. The measured PPI is stored in memory and then compared to a pre-entrainment tachycardia cycle length. The difference between the PPI and the tachycardia cycle length can be classified according to the likelihood that the entrained reentrant circuit is an actual reentrant circuit causing tachycardia or other arrhythmias. For example, if the determined difference between the PPI and the tachycardia cycle length is between 0-20 ms, the location of the sensor in the heart will be annotated on an electroanatomical timing map as green, indicating good entrainment and a very likely candidate for an active reentrant circuit. If the determined difference is between 20-40 ms, the location may be annotated as yellow, indicating a mid-level of entrainment and an unlikely candidate for an active reentrant circuit. If the determined difference is more than 40 ms, the location may be annotated as red on the electroanatomical timing map, indicating that this location of the sensor is not a candidate for an active reentrant circuit. By moving the sensor of the mapping catheter around the heart of the patient and by measuring the PPI and annotating an electroanatomical timing map of the heart, an operator can generate an enhanced electroanatomical timing map showing the most probable sites for active reentrant circuits. It is noted that other visualization techniques can be used to annotate an electroanatomical timing map and to indicate the difference between the PPI and the tachycardia cycle length. The annotation may be a line, a dot or other shape indicative of a position of the tip of the mapping/ablation catheter in the patient. It is also noted that the colours of the annotations, the sizes and the setting for what PPI difference in length triggers what annotation can be customized to the individual patient and operator. Once set by the operator, automated annotation of the measured PPIs will be performed according to the disclosed technique for each entrainment run.

Figure 6:
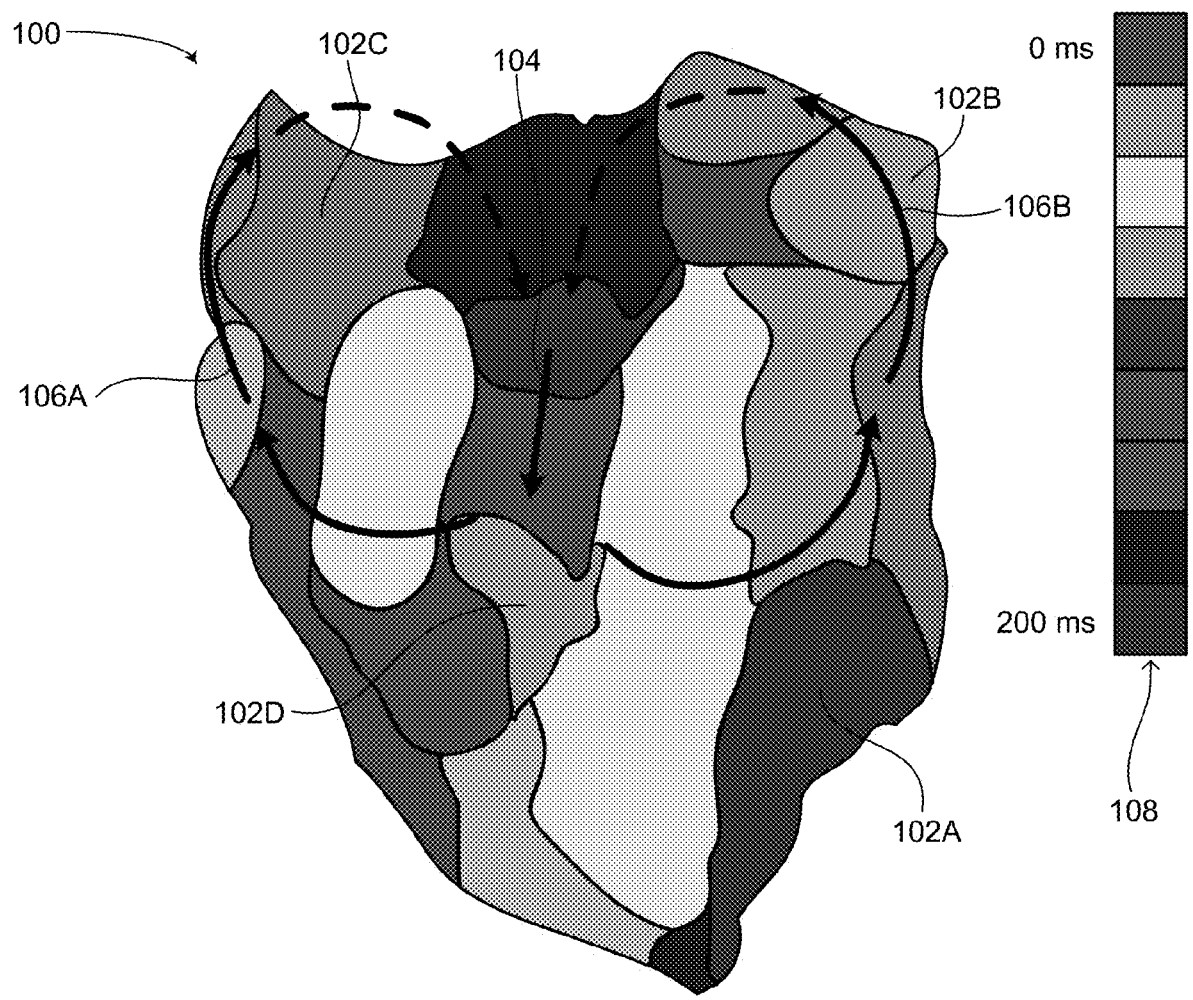
FIG. 6 is an example of a schematic electroanatomical timing map showing two possible reentrant circuits, as is known in the prior art.

Reference is now made to FIG. 6, which is an example of a schematic electroanatomical timing map showing two possible reentrant circuits, generally referenced 100, as is known in the prior art. The utility of the disclosed technique is demonstrated using FIG. 6. Shown is a schematic electroanatomical timing map of the anterior surface of the left atria showing a plurality of regions 102A, 102B, 102C and 102D of the heart representing different relative electrical conduction time ranges. Not all regions are labeled, however each region represents a different overall relative electrical conduction time. A legend 108 shows the progression of colours from a relative conduction time of 0 milliseconds (red) to a relative conduction time of 200 milliseconds (purple). The colour coding of the map gives an indication of potential reentrant circuits where early and late timing points meet in the middle, as shown by an arrow 104. Two possible reentry circuits are shown in FIG. 6. A first circuit 106A is shown around the right sided pulmonary veins, whereas a second circuit 106B is shown around the left sided pulmonary veins. Other potential reentry circuits could involve the anterior wall of the left atrial (not shown), or the circuits shown in FIG. 6 might simply by bystander circuits with the actual active reentrant circuit causing a tachycardia located elsewhere. The arrows shown used to demarcate first circuit 106A and second circuit 106B are not automatically generated by the software used to generate electroanatomical timing map 100. These arrows may be added by the medical practitioner while moving the mapping/ablation catheter around the heart of a patient and slowly building the electroanatomical timing map. As can be seen, using the electroanatomical timing map of FIG. 6, it is not possible to determine if first circuit 100A, second circuit 100B or any other circuits visible in FIG. 6 are indeed the active reentrant circuit causing a tachycardia or not.

Figure 7:
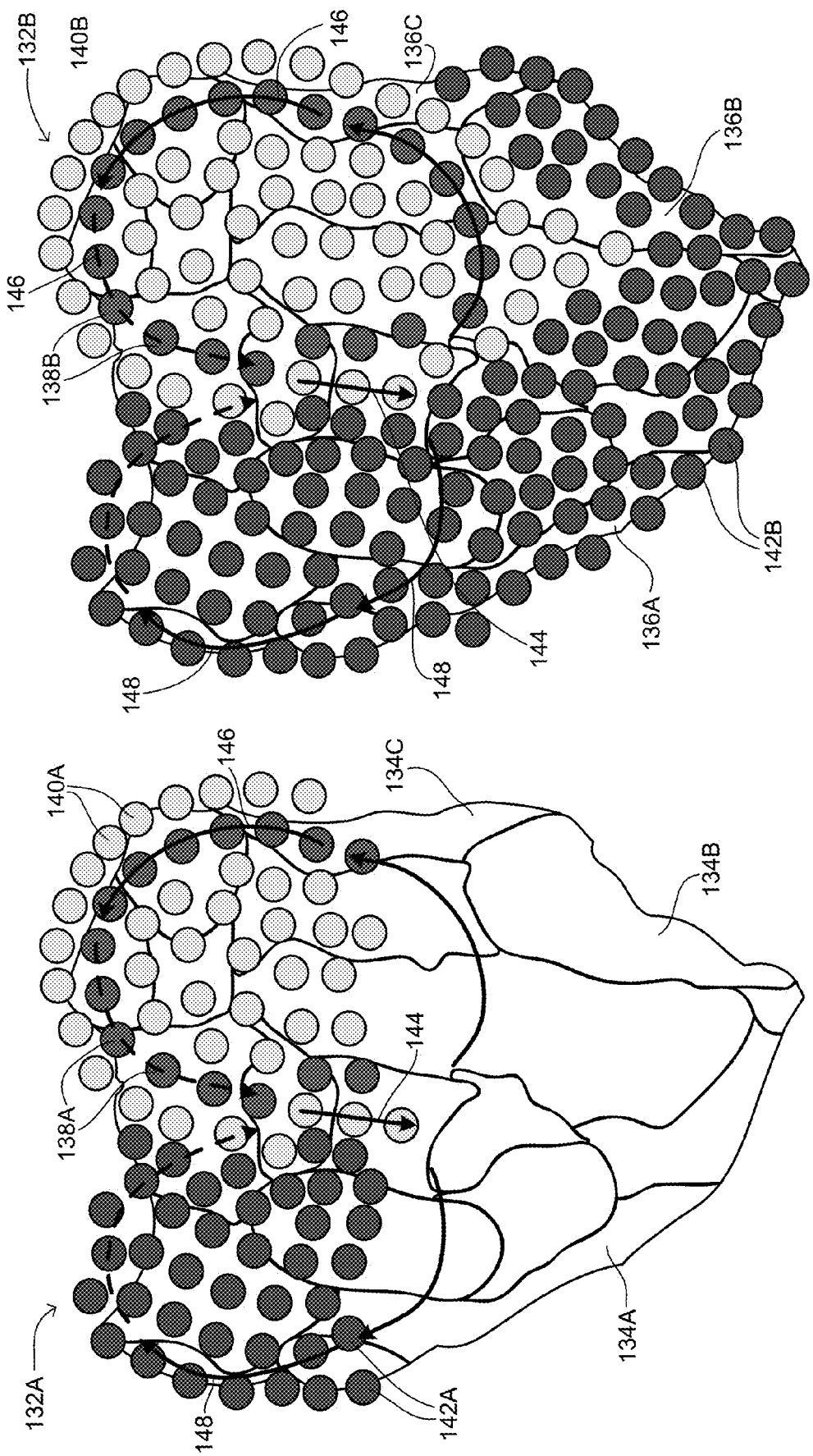
FIG. 7 is an example of the generation of an enhanced electroanatomical timing map using the annotation of the disclosed technique, constructed and operative in accordance with an embodiment of the disclosed technique.

Reference is now made to FIG. 7, which is an example of the generation of an enhanced electroanatomical timing map using the annotation of the disclosed technique, generally referenced 130, constructed and operative in accordance with an embodiment of the disclosed technique. FIG. 7 shows the same enhanced electroanatomical timing map at two different time periods, a first map 132A when the map is partially completed and a second map 132B when the map is fully completed. As described below, the enhanced electroanatomical timing map is generated by moving around a mapping/ablation catheter or sensor around the heart of a patient, similar to how the electroanatomical timing map was generated in FIG. 6. However in FIG. 7, enhanced data is presented to the user above and beyond just a map of the relative electrical conduction times of circuits within the heart. In first map 132A, shown without colour are various regions of the heart, such as regions 134A, 134B and 134C. In second map 132B, corresponding regions 136A, 136B and 136C are shown. These regions represent regions in the heart having similar relative electrical conduction times. A user may be able to request of the software program generating first map 132A and second map 132B that the standard electroanatomical timing map be shown and then these regions would be shown in colour, as was shown in FIG. 6. According to the disclosed technique, the enhanced electroanatomical timing map shows an entrainment map (the colour dots shown in FIG. 7), similar to an electroanatomical timing map, except what is shown is the difference between PPI measurements at various points within the heart and measurements of a tachycardia cycle length. The entrainment map is similar anatomically to the map shown in FIG. 6 however the information revealed is very different. As the operator, such as a clinician, physician, cardiologist and the like, moves a mapping/ablation sensor or catheter inside the heart of a patient, various areas of the heart are annotated, in this example using a colour code, to illustrate where an actual reentrant circuit might be in the heart. As the mapping/ablation sensor moves around the heart, the location of its tip is colour-coded in the entrainment map, representing the difference between the measured PPI and the tachycardia cycle length. The colour-coding in FIG. 7 is shown using dots however other symbols can be used. A green dot may represent a location with almost no difference in PPI and tachycardia cycle length, thus representing a location of high probability of being within an active reentrant circuit. A yellow dot may represent a location with some difference in PPI and tachycardia cycle length, thus representing a location of low probability of being within the active reentrant circuit. A red dot may represent a location with substantial difference in PPI and tachycardia cycle length, thus representing a location of substantially no probability of being within the active reentrant circuit. The same two potential reentrant circuits from FIG. 6 are shown in FIG. 7 as a first circuit 148 (shown as a plurality of arrows) and a second circuit 146 (also shown as a plurality of arrows). These two circuits both have early and late meeting relative conduction times at a mid-section shown by an arrow 144. As shown in first map 132A, measurement locations in the heart where the PPI has between a 0-20 ms difference with the tachycardia cycle length are shown as green dots 138A, whereas locations where the PPI difference is between 20-40 ms are shown as yellow dots 140A. Locations where the PPI difference is above 40 ms are shown as red dots 142A. First map 132A shows that the operator has only moved the mapping/ablation sensor in the upper regions of the left atrium of the heart. Second map 132B shows the entrainment map after the operator has moved the mapping/ablation sensor throughout the entire volume of the left atrium, showing measurement locations in the heart where the PPI has between a 0-20 ms difference with the tachycardia cycle length as green dots 138B, locations where the PPI difference is between 20-40 ms as yellow dots 140B and locations where the PPI difference is above 40 ms as red dots 142B. As shown in FIG. 7, second reentrant circuit 146, which is the left pulmonary vein set and anterior left atrium wall, is shown to be an active reentrant circuit, whereas first reentrant circuit 148 is merely a bystander circuit. Appropriate ablations to terminate and eliminate second reentrant circuit 146 can now be delivered to the patient, according to the disclosed technique. By recording the PPI interval difference with the tachycardia cycle length as overdrive pacing is performed in the patient's heart and annotating an entrainment map of the heart using a colour code, the location of active reentrant circuits can be easily and quickly determined and recorded, thus enabling the operator to return to these exact circuits for ablation.

It is noted that the disclosed technique can be embodied as a method as part of a software add-on utility to known software platforms used to generate electroanatomical timing maps, such as the CARTO system developed by Johnson & Johnson® and the EnSite cardiac mapping system developed by St. Jude Medical®. Such a method is described below in FIG. 8. In addition, the disclosed technique can be embodied as a system for sensing and determining the PPI of a mapping catheter and for generating an enhanced electroanatomical timing map and annotating the map as described above to generate an entrainment map.

The disclosed technique can be embodied in other manners besides the example shown in FIG. 7, wherein information about entrainment for a given circuit in an electroanatomical timing map can be used to modify the map to enhance the information made available to the operator or medical practitioner. For example, if a sensed region has very poor entrainment, the information of that region may be eliminated from the electroanatomical timing map, enabling the map to be redrawn to only show information related to areas of good entrainment. As described above, in one embodiment, the PPI measurement of a circuit can be overlaid on an electroanatomical timing map to enhance information about potential reentrant circuits. In another embodiment, a separate map can be generated showing regions of the heart which have been shown to be part of an active reentrant tachycardia circuit.

Figure 4:
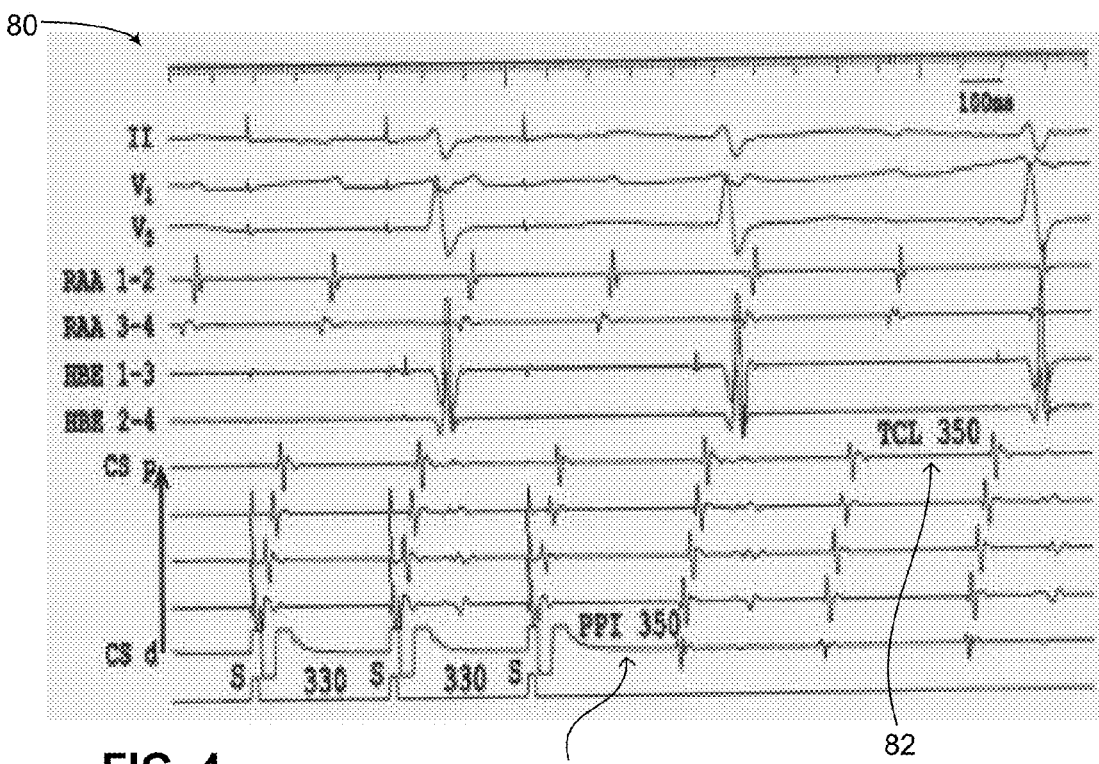
FIG. 4 is an EKG showing a reentrant circuit which is the cause of a tachycardia, as is known in the prior art.
Figure 5:
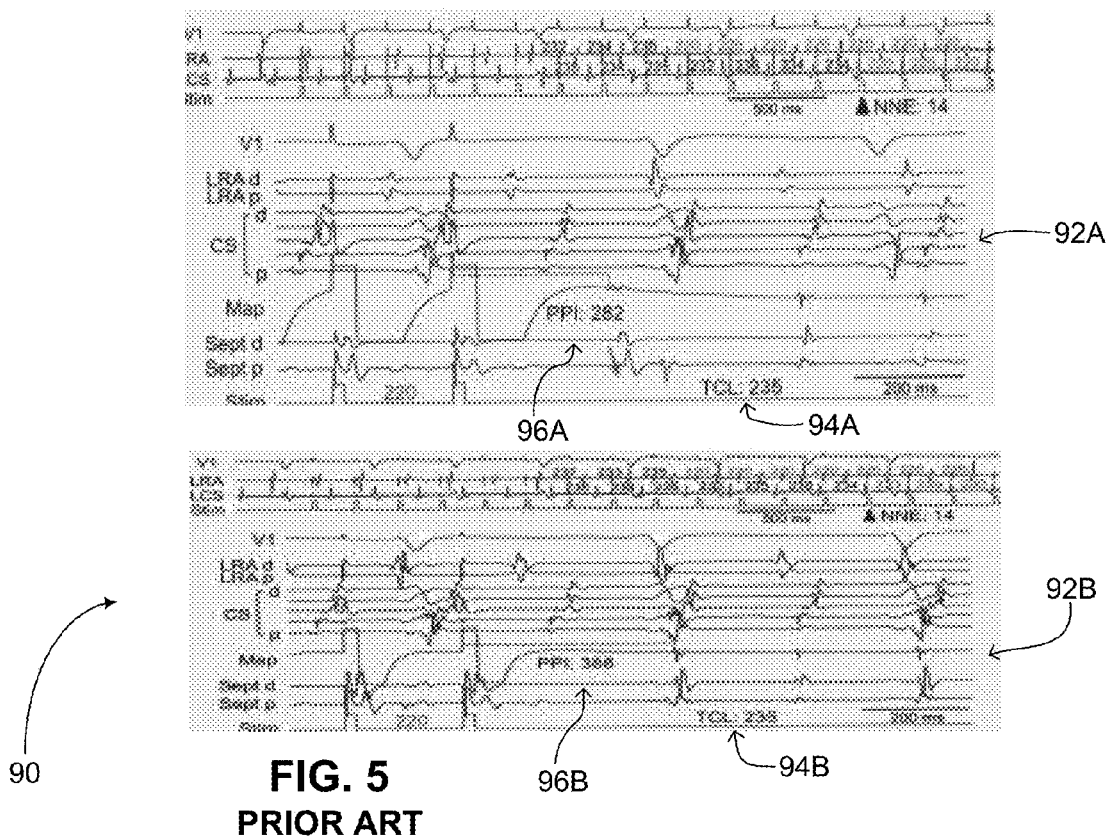
FIG. 5 is an example of two EKGs showing reentrant circuits which are not the cause of a tachycardia, as is known in the prior art.
Figure 8:
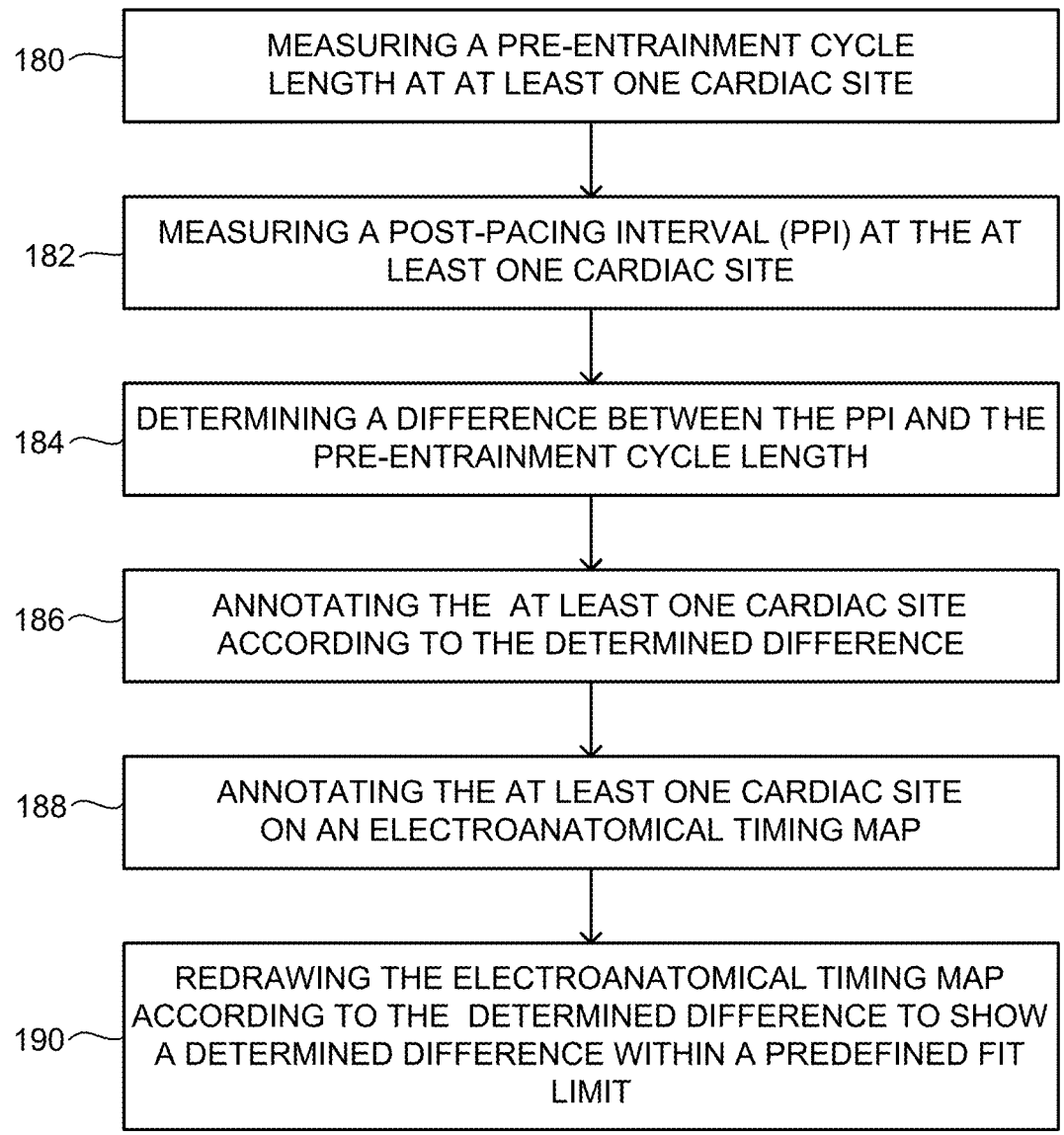
FIG. 8 is a method for generating an enhanced electroanatomical timing map using the annotation of the disclosed technique, operative in accordance with another embodiment of the disclosed technique.

Reference is now made to FIG. 8, which is a method for generating an enhanced electroanatomical timing map using the annotation of the disclosed technique, operative in accordance with another embodiment of the disclosed technique. In a procedure 180, a pre-entrainment cycle length is measured at at least one cardiac site. The pre-entrainment cycle length is the distance as typically measured in milliseconds between two local electrograms as measured on a mapping catheter or electrode at a fixed point in the heart. Electrograms are any tracings of the electrical potential of heart tissue made by means of electrodes placed directly on the heart tissue. Typically, this is measured from the onset of each electrogram or can be measured from peak to peak of each electrogram as long as the measurements are consistent. This is further described above in FIG. 7 and an example of which is shown in FIGS. 4 and 5 (which are examples are different types of electrograms). The pre-entrainment cycle length is a time period for electrical conduction to pass through the cardiac site and is stored in a memory or storage unit. The entrainment is measured at at least one cardiac site within and/or proximate to the heart where electrical conduction times can be measured. For example, the cardiac site can be the left atrium, right atrium, left ventricle, right ventricle or any of the pulmonary arteries and/or veins. Other cardiac sites are also possible including the various ostia of the heart and any sub-region of the above listed sites, for example a section of the left atrium or a part of a pulmonary artery.

In a procedure 182, a post-pacing interval (herein abbreviated PPI) is measured at the at least one cardiac site. To measure a post-pacing interval, typically the pre-entrainment cycle length is measured and then fixed rate pacing is delivered at this same site at a rate faster than the pre-existing tachycardia or arrhythmia. For example, if the pre-entrainment cycle length is 330 ms, entrainment pacing can be delivered at a cycle length of 310 ms with pacing continued until capture of the local electrogram occurs and all intracardiac electrogram channels recorded are advanced to the faster cycle length of the entrainment pacing. Then, pacing is stopped and the PPI is measured. The PPI is the distance, as typically measured in milliseconds of the time between cessation of entrainment pacing and the first electrogram recorded after the tachycardia resumes following pacing. The PPI is measured at the site where entrainment pacing is delivered and by the same catheter or probe from which entrainment pacing is delivered and is measured without moving the catheter or probe from this site.

The PPI is measured by using overdrive pacing techniques or other known techniques in the art for attempting to entrain an electrical conduction circuit in the heart. Typically overdrive pacing is at a fixed rate and is 20 ms faster than the existing tachycardia cycle length. Examples of measuring the PPI were shown above in FIGS. 4 and 5. The measured PPI may be stored in a memory or storage unit. In a procedure 184, a difference between the PPI and the pre-entrainment cycle length is determined. As described above in FIGS. 4 and 5, a difference between the PPI and the measured tachycardia cycle length can be calculated. In FIGS. 4 and 5 this difference was calculated manually as per the prior art. In procedure 184, the difference is calculated automatically using computer software accessing the measured PPI and measured pre-entrainment cycle length.

In a procedure 186, the at least one cardiac site is annotated according to the determined difference. The annotation can be a numbering representation of the actual difference or a colour or symbol representation representing different ranges of the determined difference. Other annotations are possible. The annotation can be made on a representation of the cardiac site, such as on a computer-generated image of the heart. The annotation can be executed automatically via computer software. In a procedure 188, the at least one cardiac site is annotated on an electroanatomical timing map. As was shown above in FIG. 7, different ranges of determined differences can be annotated on an electroanatomical timing map using different colours. In the case of FIG. 7, determined differences of between 0-20 ms were annotated using green dots, determined differences of between 20-40 ms were annotated using yellow dots and determined differences of more than 40 ms were annotated using red dots. The cardiac site in FIG. 7 was the left atrium. The annotation shown in FIG. 7 is merely one example and other annotation colours and/or symbols as well as other ranges per colour or symbol could have been used and is a matter of design choice. It is noted that procedure 188 is optional.

In a procedure 190, the electroanatomical timing map is redrawn according to the determined difference to show a determined difference within a predefined fit limit. The redrawn map may be referred to as an entrainment map, as shown above in FIG. 7. In one embodiment, the redrawn map may be redrawn according to the determined difference to show a minimal determined difference of less than a predefined good fit limit. In another embodiment, the redrawn map may be redrawn according to the determined difference to show a maximal determined difference over a predefined poor fit limit. Procedure 190 is an optional procedure.

The disclosed technique enables an enhanced electroanatomical timing map to be generated on the fly as an operator (such as a cardiologist or electrophysiologist) moves a mapping/ablation catheter around a cardiac site in a patient's heart. The enhanced electroanatomical timing map allows for the generation of an entrainment map which can record the precise location of an active reentry circuit. Once the entire heart has been mapped, the operator can then return to the recorded locations of the active reentry circuit or circuits and ablate them, thereby significantly increasing the chances over the prior art of ablating the proper portion of the heart for terminating a reentry circuit or circuits. The method shown in FIG. 8 can be embodied as a piece of software or a software module and can be incorporated into the software currently used to generate state-of-the-art electroanatomical timing maps. It will be appreciated by persons skilled in the art that the disclosed technique is not limited to what has been particularly shown and described hereinabove. Rather the scope of the disclosed technique is defined only by the claims, which follow.

The invention claimed is:

1. Method for determining positive entrainment sites for mapping active reentrant circuits of a reentrant tachycardia before ablation, comprising the procedures of:
   measuring a pre-entrainment cycle length of at least one cardiac site;
   measuring a post-pacing interval (PPI) at said at least one cardiac site;
   determining a difference between said PPI and said pre-entrainment cycle length;
   annotating said at least one cardiac site according to said determined difference on an electroanatomical map; and
   redrawing said electroanatomical map according to said determined difference to show said determined difference within a predefined fit limit thus annotating at least one active reentrant circuit of said reentrant tachycardia on said electroanatomical map to be ablated for terminating said at least one active reentrant circuit and thus said reentrant tachycardia.

2. The method according to claim 1, wherein said determined difference within said predefined fit limits shows a minimal determined difference of less than a predefined good fit limit.

3. The method according to claim 1, wherein said determined difference within said predefined fit limit shows a maximal determined difference over a predefined poor fit limit.

4. The method according to claim 1, wherein at least one bystander circuit is annotated so as to make evident to an operator that said at least one bystander circuit is not a positive entrainment site and is a non-active reentrant site of delayed cardiac conduction and thereby not a candidate for ablation.

5. The method according to claim 1, wherein said at least one cardiac site is selected from a list consisting of:
   a left atrium;
   a right atrium;
   a left ventricle;
   a right ventricle;
   a pulmonary artery;
   a pulmonary vein;
   an ostia of the heart; and
   a sub-region of at least one of the above.

6. The method according to claim 1, wherein said procedure of measuring said PPI comprises the procedures of:
   delivering a fixed rate pacing at said at least one cardiac site at a rate faster than a rate of a pre-existing arrhythmia; and
   stopping said fixed rate pacing and then measuring said PPI.

7. The method according to claim 1, wherein said annotating comprises an annotation representing said determined difference.

8. The method according to claim 7, wherein said annotation is selected from a list consisting of:
   a numbering;
   a color-coding; and
   a symbol.

9. The method according to claim 7, wherein said annotation is made on a representation of said at least one cardiac site.

10. The method according to claim 9, wherein said representation is a computer-generated image of a heart.

11. The method according to claim 7, wherein said annotation is executed automatically via computer software.

12. The method according to claim 1, further comprising the procedure of redrawing said electroanatomical map according to said determined difference to eliminate at least one region of said electroanatomical map showing poor entrainment.

* * * * *